United States Patent [19]

Engel et al.

[11] 3,987,197

[45] Oct. 19, 1976

[54] 3-(2'-FLUORO-4-BIPHENYLYL)-BUTYRIC ACID AND SALTS THEREOF

[75] Inventors: Wolfhard Engel; Helmut Teufel; Ernst Seeger; Josef Nickl; Günther Engelhardt, all of Biberach an der Riss, Germany

[73] Assignee: Boehringer Ingelheim GmbH, Ingelheim am Rhein, Germany

[22] Filed: May 14, 1975

[21] Appl. No.: 577,170

Related U.S. Application Data

[63] Continuation-in-part of Ser. No. 387,801, Aug. 13, 1973, abandoned.

[30] Foreign Application Priority Data

| Aug. 17, 1972 | Germany | 2240441 |
| Dec. 18, 1972 | Germany | 2261912 |
| Jan. 5, 1973 | Germany | 2300402 |
| Feb. 28, 1973 | Germany | 2309914 |
| May 3, 1973 | Germany | 2322195 |

[52] U.S. Cl. .................. 424/316; 260/247.2 R; 260/268 R; 260/286 R; 260/501.16; 260/515 A; 260/592; 260/618 D; 260/649 F; 424/317

[51] Int. Cl.$^2$ .................................. C07C 63/333
[58] Field of Search .... 260/515 A, 501.16, 247.2 R, 260/268 R; 424/316, 317

[56] References Cited
UNITED STATES PATENTS

| 3,624,142 | 11/1971 | Shen et al. | 260/515 |
| 3,755,427 | 8/1973 | Adams et al. | 260/515 |

FOREIGN PATENTS OR APPLICATIONS

| 56/65 | 2/1965 | Ireland | 260/515 A |

*Primary Examiner*—Jane S. Myers
*Attorney, Agent, or Firm*—Hammond & Littell

[57] ABSTRACT

3-(2'-Fluoro-4-biphenylyl)-butyric acid and salts thereof formed with inorganic or organic bases; the compound as well as its salts are useful as antiphlogistics and antirheumatics.

5 Claims, No Drawings

3-(2'-FLUORO-4-BIPHENYLYL)-BUTYRIC ACID AND SALTS THEREOF

This is a continuation-in-part of copending application Serial No. 387,801, filed August 13, 1973, now abandoned.

This invention relates, to the novel compound 3-(2'-fluoro-4-biphenylyl)-butyric acid and salts thereof formed with inorganic or organic bases, as well as to a method of preparing these compounds.

3-(2'-Fluoro-4-biphenylyl)-butyric acid may be prepared by reacting a biphenyl derivative of the formula

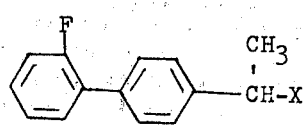

wherein X is hydroxyl, halogen or acyloxy, with a 1,1-dihaloethylene, preferably 1,1-dichloro-ethylene, in sulfuric acid which advantageously contains boron trifluoride, and hydrolyzing the intermediate by addition of water.

The starting compounds of the formula I are, for the most part, known compounds or may be readily prepared by known methods.

For instance, a compound of the formula I wherein X is hydroxyl may be obtained by reducing the ketone of the formula

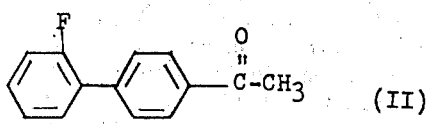

with a complex metal hydride, especially with sodium borohydride.

A compound of the formula I wherein X is halogen or acyloxy may be prepared from the corresponding compound of the formula I wherein X is hydroxyl by conventional methods, such as by treatment with a hydrohalic acid, a phosphorus halide or a thionyl halide, or by acylation, respectively.

The ketone of the formula II, in turn, may be obtained by reacting 2-fluoro-biphenyl with acetyl chloride in the presence of anhydrous aluminum chloride.

The above method yields 3-(2'-fluoro-4-biphenylyl)-butyric acid as a racemate or racemic mixture which may subsequently be easily separated into its optically active components by fractional crystallization of its salts with an optically active base. The racemate separation with quinine has proved to be particularly well suited.

3-(2'-Fluoro-4-biphenylyl)-butyric acid forms salts with inorganic or organic bases. Examples of non-toxic, pharmacologically acceptable salts are those formed with diethanolamine, morpholine, cyclohexylamine or piperazine.

The following examples illustrate the present invention and will enable others skilled in the art to understand it more completely. It should be understood, however, that the invention is not limited solely to the particular examples given below.

EXAMPLE 1

3-(2'-Fluoro-4-biphenylyl)-butyric acid

A solution of 0.25 mol of 1-(2'-fluoro-4-biphenylyl)-1-ethanol (m.p. 86°–87° C) in 242 gm (2.5 mol) of 1,1-dichloroethylene was added dropwise to 540 gm of 90% sulfuric acid containing 8% of borontrifluoride at 0° C, accompanied by stirring. The resulting mixture was stirred for two hours more at room temperature, was then poured into ice water, and the oil which thereupon separated out was taken up in ether. The ethereal solution was extracted with 500 ml of aqueous 10% sodium hydroxide, the alkaline aqueous extract was acidified with aqueous 15% hydrochloric acid, the precipitate formed thereby was taken up in ether, the ethereal solution was dried with sodium sulfate, and the ether was distilled off, leaving 42% of theory of the compound of the formula

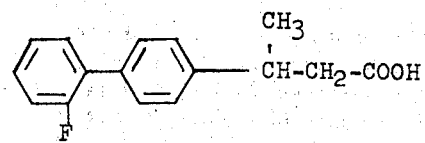

which had a melting point of 90°–99° C after recrystallization from cyclohexane.

The cyclohexylamine salt of the acid had a melting point of 162°–163° C.

EXAMPLE 2

Separation of racemic 3-(2'-fluoro-4-biphenylyl)-butyric acid into its optically active components 77.5 gm (0.3 mol) of racemic 3-(2'-fluoro-4-biphenylyl)-butyric acid were dissolved in 1.5 liters of ethanol, and the solution was admixed with a solution of 97.2 gm (0.3 mol) of quinine in 1.5 liters of ethanol. The colorless precipitate (A) formed thereby was collected by vacuum filtration and recrystallized fifteen times from a total of 30 liters of ethanol, yielding 5.5 gm of dextro-rotatory 3-(2'-fluoro-4-biphenylyl)-butyric acid, $[\alpha]_D^{20} = +34.5°$, m.p. 87°–88° C (recrystallized from cyclohexane).

The filtrate was freed from solvent by evaporation, the residue was taken up in 500 ml of hot methanol, the resulting solution was allowed to cool, and the precipitate formed thereby was collected by vacuum filtration and discarded. The filtrate was treated with methanol in the same manner four times more, the last evaporation residue was dissolved in 500 ml of warm ethyl acetate, the solution was allowed to cool, and the precipitate formed thereby was collected by vacuum filtration and recrystallized from about 500 ml of ethyl acetate, yielding 2.3 gm of levo-rotatory 3-(2'-fluoro-4-biphenylyl)-butyric acid, $[\alpha]_D^{20} = -33.5°$, m.p. 85°–87° C (recrystallized from cyclohexane).

The compounds of the present invention, that is, 3-(2'-fluoro-4-biphenylyl)-butyric acid and non-toxic salts thereof, have useful pharmacodynamic properties. More particularly, the compounds of the instant invention exhibit very effective antiphlogistic and antirheumatic activities in warm-blooded animals, such as rats.

The compounds were tested by standard test methods for their anti-exudative effects on the kaolin edema and carrageenin edema of the hind paws of the rat and for their acute toxicity by oral administration to rats.

The kaolin edema was induced according to the method of Hillebrecht [Arzneimitted-Forsch. 4, 607 (1954)] by subplantary injection of 0.05 ml of a 10% suspension of kaolin in a 0.85% sodium chloride solution. The measurement of the thickness of the paws was done by using the technique of Doepfner and Cerletti [Int. Arch. Allergy. Immunol. 12, 89 (1958)].

Male FW 49-rats of an average weight of 120–150 gm were orally treated with the test compounds 30 minutes before inducement of the edema with the aid of an esophageal tube. Five hours after the provocation of the edema the averaged values of the swelling caused in the paws of the rats treated with the compounds were compared with those values measured on blind-treated control animals. By graphic extrapolation the dose leading to a 35% reduction of the swelling ($ED_{35}$) was calculated from the percent reduction values measured by administration of different doses.

The provocation of the carrageenin edema was effected according to the method of Winter et al [Proc. Soc. exp. Biol. Med. 111, 544 (1962)] by subplantary injection of 0.05 ml of a 1% solution of carrageenin in a 0.85% solution of sodium chloride. The test compounds were orally administered 60 minutes before the provocation of the edema.

For the calculation of the reductive effect on the edema the values measured three hours after the provocation of the edema were used. All the other details were the same as described above in the case of the kaolin edema.

After oral administration to male and female FW 49-rats (ratio 1:1) having an average body weight of 135 gm, the acute toxicity ($LD_{50}$) was determined. The substances were administered orally as trituration in tylose.

The calculation of the $LD_{50}$-values was effected, as far as possible, according to the method of Litchfield and Wilcoxon, based on the percentage of animals which died within 14 days after administration of the different doses.

The therapeutic index, as a measure for the therapeutic usefulness, was calculated by forming the quotient of the $LD_{50}$-value and the $ED_{35}$-value derived from the tests for anti-exudative activity against the kaolin and carrageenin edema.

The following table shows the results obtained from these tests, were

A = 3-(2'-fluoro-4-biphenylyl)-butyric acid.

For pharmaceutical purposes the compound according to the present invention is administered to warm-blooded animals perorally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effection antiphlogistic dosage unit of the compounds according to the present invention is from 0.83 to 6.67 mgm/kg body weight, preferably 1.33 to 5.0 mgm/kg body weight. The daily dose rate is from 1.66 to 16.7 mgm/kg body weight, preferably 2.5 to 10 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 3

Tablets

The tablet composition is compounded from the following ingredients:

| | |
|---|---|
| 3-(2'-Fluoro-4-biphenylyl)-butyric acid | 50.0 parts |
| Corn starch | 247.0 parts |
| Polyvinylpyrrolidone | 10.0 parts |
| Magnesium stearate | 3.0 parts |
| Total | 310.0 parts |

Preparation:

The butyric acid compound and the corn starch are intimately admixed with each other, the mixture is granulated with an aqueous 14% solution of the polyvinylpyrrolidone through a 1.5 mm-mesh screen, the granulate is dried at 45° C and again passed through the screen, the dry granulate is admixed with the magnesium stearate, and the composition is compressed into 310 mgm-tablets in a conventional tablet making machine. Each tablet contains 50 mgm of the butyric acid compound and is an oral dosage unit composition with effective antiphlogistic and antirheumatic action.

EXAMPLE 4

Coated pills

The pill core composition is compounded from the following ingredients:

| | |
|---|---|
| 3-(2'-Fluoro-4-biphenylyl)-butyric acid | 100.0 parts |
| Corn starch | 170.0 parts |
| Gelatin | 8.0 parts |
| Talcum | 18.0 parts |
| Magnesium stearate | 4.0 parts |
| Total | 300.0 parts |

TABLE

| Compound | kaolin edema $ED_{35}$ per os mgm/kg | carrageenin edema $ED_{35}$ per os mgm/kg | antiexudative effect $ED_{35}$ mgm/kg* | acute toxicity in the rat $LD_{50}$ per os mgm/kg | confidence limits (95% probability) | Therapeutic Index ratio of toxic and antiexudative effect $LD_{50}/ED_{35}$* |
|---|---|---|---|---|---|---|
| A | 19 | 10.5 | 14.8 | 540 | 422 – 691 | 36.5 |

*arithmetically averaged value from $ED_{35}$ kaolin edema and $ED_{35}$ carrageenin edema Preparation:

The butyric acid compound and the corn starch are intimately admixed with each other, the mixture is granulated with an aqueous 10% solution of the gelatin through a 1.5 mm-mesh screen, the granulate is dried at 45° C and again passed through the screen, the dry granulate is admixed with the talcum and the magnesium stearate, and the composition is compressed into 300 mgm-pill cores which are subsequently coated with a thin shell consisting essentially of a mixture of sugar and talcum and finally polished with beeswax. Each coated pill contains 100 mgm of the butyric acid compound and is an oral dosage unit composition with effective anti-phlogistic and antirheumatic action.

EXAMPLE 5

Gelatin capsules

The capsule filler composition is compounded from the following ingredients:

| | |
|---|---|
| 3-(2'-Fluoro-4-biphenylyl)-butyric acid | 200.0 parts |
| Corn starch | 190.0 parts |
| Colloidal silicic acid | 6.0 parts |
| Magnesium stearate | 4.0 parts |
| Total | 400.0 parts |

Preparation:

The ingredients are intimately admixed with each other, and 400 mgm-portions of the mixture are filled into No. 1 gelatin capsules. Each capsule contains 200 mgm of the butyric acid compound and is an oral dosage unit composition with effective antiphlogistic and antirheumatic action.

EXAMPLE 6

Suppositories

The suppository composition is compounded from the following ingredients:

| | |
|---|---|
| 3-(2'-Fluoro-4-biphenylyl)-butyric acid | 200.0 parts |
| Suppository base (e.g. cocoa butter) | 1450.0 parts |
| Total | 1650.0 parts |

Preparation:

The finely pulverized butyric acid compound is blended with the aid of an immersion homogenizer into the suppository base which had previously been melted and cooled to 40° C. 1650 mgm-portions of the composition are poured into cooled suppository molds and allowed to harden therein. Each suppository contains 200 mgm of the butyric acid compound and is a rectal dosage unit composition with effective antiphlogistic and antirheumatic action.

EXAMPLE 7

Suspension

The suspension is compounded from the following ingredients:

| | |
|---|---|
| 3-(2'-Fluoro-4-biphenylyl)-butyric acid | 4.0 parts |
| Dioctyl sodium sulfosuccinate (DONSS) | 0.02 parts |
| Benzoic acid | 0.1 parts |
| Sodium cyclamate | 0.2 parts |
| Colloidal silicic acid | 1.0 parts |
| Polyvinylpyrrolidone | 0.1 parts |
| Glycerin | 25.0 parts |
| Flavoring | 0.1 parts |
| Distilled water   g.s.ad | 100.0 parts by vol. |

Preparation:

The DONSS, the benzoic acid, the sodium cyclamate and the polyvinylpyrrolidone are successively dissolved in a sufficient amount of distilled water at 70° C, and the glycerin and colloidal silicic acid are added to the solution. The mixture is cooled to room temperature, the finely pulverized butyric acid compound is suspended therein by means of an immersion homogenizer, the flavoring is added, and the composition is diluted with additional distilled water to the indicated volume. 5 ml of the resulting aqueous suspension contain 200 mgm of the butyric acid compound and are an oral dosage unit composition with effective antiphlogistic and antirheumatic action.

EXAMPLE 8

Gelatin capsules with combination of active ingredients

The capsule filler composition is compounded from the following ingredients:

| | |
|---|---|
| 3-(2'-Fluoro-4-biphenylyl)-butyric acid | 400.0 parts |
| Corn starch | 100.0 parts |
| 5,11-Dihydro-11-[(4-methyl-1-piperazinyl)-acetyl]-6H-pyrido[2,4-b][1,4]benzodiazepin-6-one dihydrochloride | 25.0 parts |
| Colloidal silicic acid | 6.0 parts |
| Magnesium stearate | 4.0 parts |
| Total | 535.0 parts |

Preparation:

The ingredients are intimately admixed with each other, and 535 mgm-portions of the mixture are filled into No. 0 gelatin capsules. Each capsule contains 400 mgm of the butyric acid compound and 25 mgm of the pyridobenzodiazepinone compound and is an oral dosage unit composition with effective antiphlogistic and antirheumatic action.

The amount of active ingredient in these illustrative examples may be varied to achieve the dosage unit range set forth above, and the amounts and nature of the inert phaarmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:
1. 3-(2'-Fluoro-4-biphenylyl)-butyric acid or a nontoxic, pharmacologically acceptable salt thereof with an inorganic or organic base.
2. The compound of claim 1 which is 3-(2'-fluoro-4-biphenylyl)-butyric acid.
3. The compound of claim 1 which is the cyclohexylamine salt of 3-(2'-fluoro-4-biphenylyl)-butyric acid.
4. An antiphlogistic and antirheumatic pharmaceutical dosage unit composition consisting essentially of an inert pharmaceutical carrier and an effective antiphlogistic and antirheumatic amount of a compound of claim 1.
5. The method of combatting inflamation and rheumatism in a warm-blooded animal, which comprises administering to said animal an effective antiphlogistic and antirheumatic amount of a compound of claim 1.

* * * * *

UNITED STATES PATENT OFFICE
CERTIFICATE OF CORRECTION

Patent No. 3,987,197    Dated October 19, 1976

Inventor(s) WOLFGANG ENGEL, HELMUT TEUFEL, ERNST SEEGER, JOSEF HECKL and GUNTHER ENGELHARDT It is certified that error appears in the above-identified patent and that said Letters Patent are hereby corrected as shown below:

Col. 2 line 35    "90-99°C" should read -- 97-99°C --

Col. 3 line 55    "were" should read -- where --

Col. 4 line 10    "affection" should read -- effective --

Col. 6 line 3    "g.s.ad." should read -- q.s.ad. --

Col. 6 line 44    "phaarma" should read -- pharma --

Signed and Sealed this

Fourth Day of January 1977

[SEAL]

Attest:

RUTH C. MASON
Attesting Officer

C. MARSHALL DANN
Commissioner of Patents and Trademarks